United States Patent
Tei et al.

(10) Patent No.: US 12,378,199 B2
(45) Date of Patent: Aug. 5, 2025

(54) RIGIDIFIED PENTADENTATE CHELATING AGENTS USEFUL FOR THE $[Al^{18}F]^{2+}$ LABELLING OF BIOMOLECULES

(71) Applicant: UNIVERSITÀ DEGLI STUDI DEL PIEMONTE ORIENTALE "A. AVOGADRO", Vercelli (IT)

(72) Inventors: Lorenzo Tei, Turin (IT); Jonathan Martinelli, Alessandria (IT)

(73) Assignee: UNIVERSITÀ DEGLI STUDI DEL PIEMONTE ORIENTALE "A. AVOGADRO", Vercelli (IT)

( * ) Notice: Subject to any disclaimer, the term of this patent is extended or adjusted under 35 U.S.C. 154(b) by 707 days.

(21) Appl. No.: 17/439,536

(22) PCT Filed: Mar. 17, 2020

(86) PCT No.: PCT/IB2020/052409
§ 371 (c)(1),
(2) Date: Sep. 15, 2021

(87) PCT Pub. No.: WO2020/188478
PCT Pub. Date: Sep. 24, 2020

(65) Prior Publication Data
US 2022/0153697 A1     May 19, 2022

(30) Foreign Application Priority Data
Mar. 18, 2019 (IT) ........................ 102019000003905

(51) Int. Cl.
| | |
|---|---|
| *C07D 211/26* | (2006.01) |
| *A61K 51/04* | (2006.01) |
| *C07C 229/16* | (2006.01) |
| *G01N 33/60* | (2006.01) |

(52) U.S. Cl.
CPC ........ *C07D 211/26* (2013.01); *A61K 51/0482* (2013.01); *C07C 229/16* (2013.01); *G01N 33/60* (2013.01); *C07C 2601/14* (2017.05)

(58) Field of Classification Search
CPC . C07D 211/26; A61K 51/0482; C07C 229/16; G01N 33/60
USPC .......................................................... 424/1.89
See application file for complete search history.

(56) References Cited

U.S. PATENT DOCUMENTS

| | | |
|---|---|---|
| 5,292,938 A | 3/1994 | Mease et al. |
| 5,334,729 A | 8/1994 | Mease et al. |
| 2014/0017168 A1 | 1/2014 | D'Souza et al. |

FOREIGN PATENT DOCUMENTS

| | | |
|---|---|---|
| WO | 9114459 A1 | 10/1991 |
| WO | 2016065435 A3 | 5/2016 |

OTHER PUBLICATIONS

Shetty et al. Chem. Commun. 2011, 47, 9732-9734. (Year: 2011).*
Chong et al. J. Org. Chem. 2001, 66, 7745-7750. (Year: 2001).*
International Search Report, issued in PCT/IB2020/052409, mailed May 27, 2020, Rijswijk, NL.
Cleeren Frederik et al., Direct fluorine-18 labeling of heat-sensitive biomolecules for positron emission tomography imaging using the Al18F-RESCA method, Nature Protocols, Sep. 24, 2018, pp. 2330-2347, vol. 13, No. 10, Nature Publishing Group, GB.
McBride, W.J. et al., Radiofluorination using aluminum-fluoride (Al18F), Ejnmmi Research, May 8, 2013, vol. 3, Article 36, Springer.
Laverman P. et al., Al18F labeling of peptides and proteins, Journal of Labelled Compounds and Radiopharmaceuticals, Jan. 10, 2014, pp. 219-223, vol. 57, Issue 4, John Wiley & Sons, Ltd.
McBride, W.J. et al., New Lyophilized Kit for Rapid Radiofluorination of Peptides, Bioconjugate Chemistry, Jan. 25, 2012, pp. 538-547, vol. 23, Issue 3, ACS Publications, US.
Cleeren F. et al., New Chelators for Low Temperature Al18F-Labeling of Biomolecules, Bioconjugate Chemistry, Feb. 2, 2016, pp. 790-798, vol. 27, Issue 3, ACS Publications, US.

(Continued)

*Primary Examiner* — Michael G. Hartley
*Assistant Examiner* — Sean R Donohue
(74) *Attorney, Agent, or Firm* — Valauskas Corder LLC

(57) ABSTRACT

Rigidified pentadentate chelating agents of Formulae (I) and (II), which are useful for the $[Al^{18}F]^{2+}$ labelling of biomolecules are provided. The rigidified pentadentate chelating agents are used to form coordination complexes with $[Al^{18}F]^{2+}$, which are particularly advantageous for use as tracers in molecular imaging techniques.

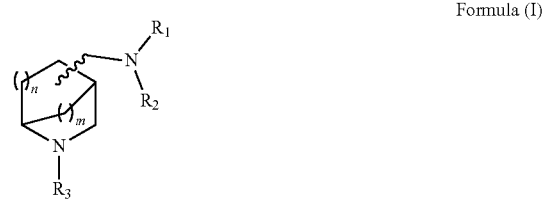

Formula (I)

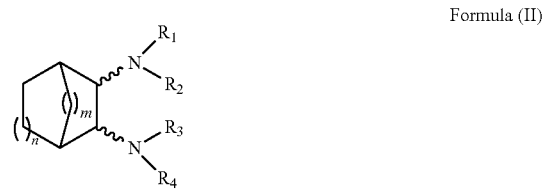

Formula (II)

14 Claims, No Drawings

(56) References Cited

OTHER PUBLICATIONS

Cleeren F. et al., Al18F-Labeling Of Heat-Sensitive Biomolecules for Positron Emission Tomography Imaging, Theranostics, Jul. 14, 2017, pp. 2924-2939, vol. 7, Issue 11, Ivyspring International Publisher, AU.

Guijarro D. et al., Enantioselective Addition of Dialkylzinc Reagents to N-(Diphenylphosphinoyl) Imines Promoted by 2-Azanorbornylmethanols, Journal of Organic Chemistry, Mar. 28, 1998, pp. 2530-2535, vol. 63, Issue 8, ACS Publications, US.

Hatano K. et al., Optical resolution of trans-Bicyclo[2.2.1]heptane-2,3-diamine: Chiral Recognition in the Crystal of Its Complex with (2R,3R)-O,O'-Dibenzoyltartaric Acid, Journal of the Chemical Society, Perkin Transactions 2, Jan. 1, 1994, pp. 579-584, Issue 3, Royal Society of Chemistry, GB.

\* cited by examiner

RIGIDIFIED PENTADENTATE CHELATING AGENTS USEFUL FOR THE $[Al^{18}F]^{2+}$ LABELLING OF BIOMOLECULES

CROSS-REFERENCE TO RELATED APPLICATIONS

This application is a U.S. National Phase filing of PCT International Patent Application No. PCT/IB2020/052409, having an international filing date of Mar. 17, 2020, which claims priority to Italian Patent Application No. 102019000003905, filed Mar. 18, 2019 each of which is hereby incorporated by reference in its entirety.

FIELD OF THE INVENTION

The present invention relates to a new class of chemical compounds useful as tracers for positron emission tomography (PET).

BACKGROUND OF THE INVENTION

In recent decades, imaging in the medical field has seen an extraordinary expansion as a result of major technological developments in the various ways of molecular imaging in vivo. These include positron emission tomography (PET), which plays a prominent role. The development of new and increasingly effective contrast agents and tracers has allowed considerable results to be achieved in the diagnostic field. The extraordinary results of research into cellular and molecular biology and knowledge of the genome have in fact resulted in an increasing knowledge of the molecular mechanisms which are at the heart of the outbreak and progression of various illnesses. Molecular imaging aims to integrate these two pathways to become medical imaging in the era of molecular and personalized medicine. The PET tracer most commonly used for the study of the glucose metabolism in neoplastic diseases is fluorodeoxyglucose ($^{18}$F-FDG). However, the continued identification of new tumor markers has made it necessary to develop new tracers which can be efficient and specific for early diagnosis of tumor diseases. Furthermore, in the era of personalized medicine, understanding the molecular mechanisms which form the basis of a particular disease also allows targeted therapies to be developed.

One of the main problems linked to the use of fluorinated tracers is that, in the vast majority of cases, $^{18}F^-$ is bonded to a small organic molecule by means of an aliphatic or aromatic nucleophilic substitution reaction which requires various synthesis steps. $^{18}F^-$ is also obtained as an aqueous solution by means of proton irradiation of $[^{18}O]H_2O$, which considerably reduces the nucleophilicity of the $F^-$ ions. Long drying steps, anhydrous aprotic solvents and high temperatures are required to increase the nucleophilicity. However, in the field of PET tracers, there is a continuing need to find new solutions for rapidly and efficiently introducing $^{18}F$ into complex and sensitive biomolecules.

Using an Al—$^{18}F$ bond by means of complexation with an appropriate chelating agent is a relatively recent method which has considerable potential. In this method, $^{18}F^-$ is firmly bonded to $Al^{3+}$ in order to form $[AlF]^{2+}$ ($F^{[18]}$—$Al^{++}$; (18F)fluoranylaluminum(2+)), which can be chelated by a suitable polydentate ligand. If the chelating agent contains a further reactive functional group for stable conjugation with the biomolecules, it is thus possible to implement direct labelling of the molecule. Aluminum forms octahedral complexes, and therefore a pentadentate chelating agent which thus leaves only one binding site available for $^{18}F^-$ is preferable.

McBride et al. (EJNMMI Res. 2013, 3, 36-47, US 2014/0017168 A1) were the first to explore the $Al^{18}F$ method, identifying the pentadentate chelating agent 1,4,7-triazacyclononane-1,4-diacetate (NODA) as the best among those tested.

It was demonstrated that the most stable aluminum complexes are based on multidentate ligands having 2-3 groups of negatively charged oxygen donors. The first clinical study to use a peptide labeled with $[Al^{18}F]^{2+}$ is P. Laverman et al., J. Labelled Comp. Radiopharm. 2014, vol. 57, issue 4, pages 219-223.

In systems in which NODA is conjugated with peptides of various types, a kit was also developed (McBride et al. Bioconjug Chem. 2012, 23, 538-47) which contains aluminum, a radioprotector (ascorbic acid), a non-volatile buffer (potassium biphthalate) and a stabilizing agent (trehalose), by means of which kit the authors were able to label a NODA-peptide system with fluorine-18 with high yields.

However, even though these macrocyclic chelating agents demonstrate considerable potential, the high temperature required for the complexation reaction (>100° C.) represents a limitation to the widespread application of this radiolabelling approach, particularly in the presence of biomolecules that are sensitive to high temperatures.

Bormans and co-authors developed some pentadentate chelating agents based on ethylene diamine and 1,2-cyclohexylene diamine which allowed efficient complexation of $[Al^{18}F]^{2+}$ at a moderate temperature (<40° C.) F. Cleeren et al Bioconjugate Chem. 2016, 27, 790-798; Theranostics 2017, 7 (11), 2924-2939; Nature Prot. 2018, 13, 2330-2347; WO/2016/065435). In particular, the pentadentate chelating agents used by Bormans and co-authors are derived from EDTA and CDTA using one acetic arm less. Using these systems, it is possible to label nanobodies with $[Al^{18}F]^{2+}$ at ambient temperature and with good yields.

U.S. Pat. No. 5,334,729 discloses polyaminocarboxylate derivates of trans-1,2-diaminocyclohexane for PET or SPECT applications. This document highlights the rigidity imposed by cyclohexane on the structure of the complexes in order to improve the stability thereof. However, the chelating agents cited in U.S. Pat. No. 5,334,729 always contain 6 donor atoms and are therefore not suitable for the complexation of $[Al^{18}F]^{2+}$ because, once complexed, the Al(III) would not have space to bond the fluoride and therefore the labelling yields would be low.

SUMMARY OF THE INVENTION

In order to improve the pentadentate chelating agents described in the prior art, both in terms of labelling characteristics and in terms of stability in physiological conditions, the present invention provides new rigidified pentadentate chelating agents for the $[Al^{18}F]^{2+}$ labelling of biomolecules, which are suitable for use as PET tracers.

DETAILED DESCRIPTION

The chelating agents of the invention are represented by formulae (i) and (ii), illustrated hereinafter:

Formula (I)

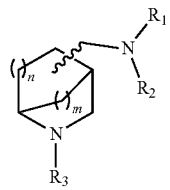

wherein n is an integer selected from 0, 1 and 2;

m is an integer selected from 0, 1 and 2;

$R_1$, $R_2$ and $R_3$ are selected from the group consisting of $CH_2CO-Z$ and $CH_2Ar$, wherein Z is selected from the group consisting of OH, NH—OH and $N(CH_3)(OH)$, and wherein Ar is an aromatic substituent of formula

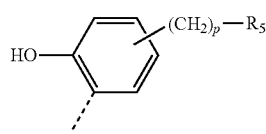

(the dotted line indicates the attachment point to the nitrogen of the main ring; this means that, in the aromatic substituent, OH is in position 2), wherein p is an integer from 0 to 6 and $R_5$ is selected from the group consisting of —H, —COOH, —NH$_2$, —NCS, —SH, Formula (II)

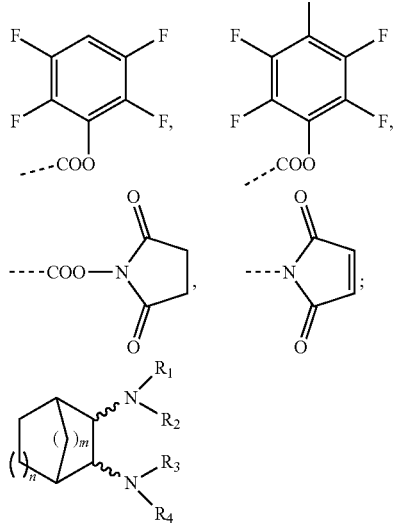

wherein n is an integer selected from 0, 1 and 2;

m is an integer selected from 0, 1 and 2;

one of $R_1$, $R_2$ and $R_3$ has the formula —CH$_2$Ar, wherein Ar is an aromatic substituent of formula

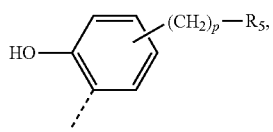

wherein p is an integer from 0 to 6 and $R_5$ is selected from the group consisting of —H, —COOH, —NH$_2$, —NCS, —SH,

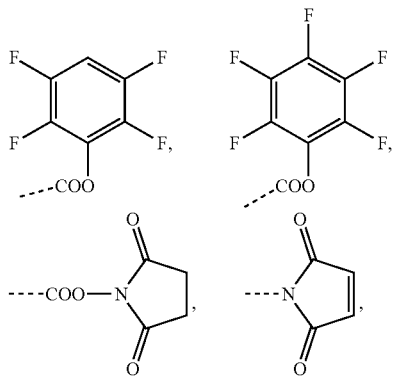

and wherein the other two of $R_1$, $R_2$ and $R_3$ are independently of one another —CH$_2$CO—Z, wherein Z is selected from the group consisting of —OH and —NH—OH, and —N(CH$_3$)(OH); $R_4$ is selected from the group consisting of: H, cyclic aliphatic substituents having from 3 to 8 carbon atoms optionally bearing a functional group selected from —COOH, —NH$_2$, —NCS, —SH,

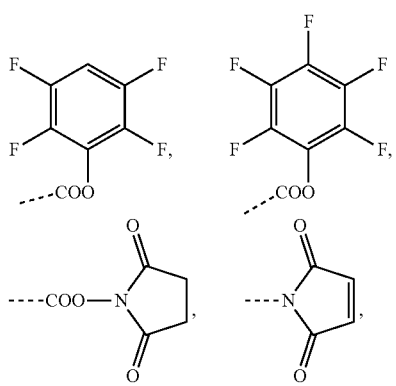

non-cyclic aliphatic substituents having from 1 to 10 carbon atoms optionally terminated with a functional group selected from —COOH, —NH$_2$, —NCS, —SH,

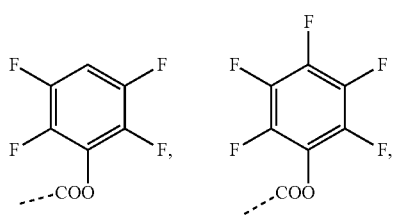

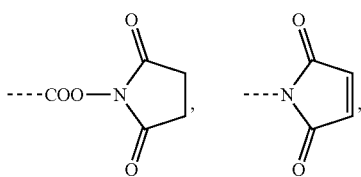

and aromatic groups Ar as defined above;

wherein formulae (I) and (II) include both R/S isomers and cis/trans isomers.

Preferred compounds included in the scope of the present invention include:

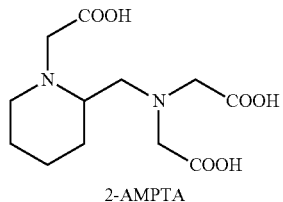

2-AMPTA

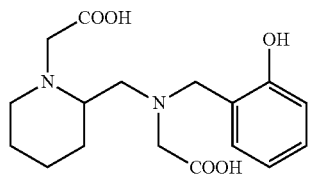

2-AMPDA-HB

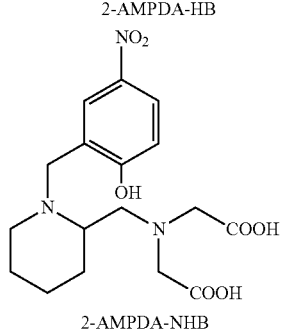

2-AMPDA-NHB

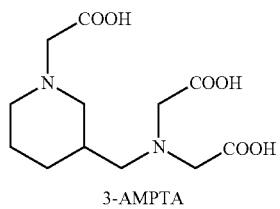

3-AMPTA

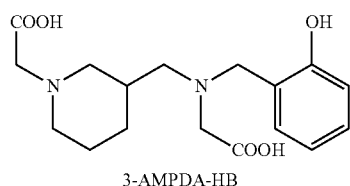

3-AMPDA-HB

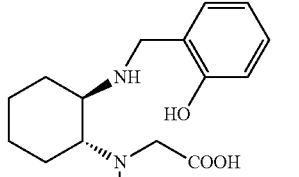

trans-CDHB-DA

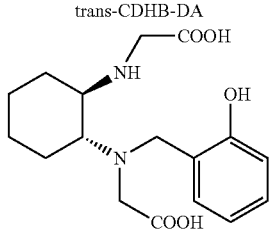

trans-CDDA-HB

The scope of the present invention also includes coordination complexes comprising a chelating agent of Formula (I) or (II) as defined above and $[AlF]^{2+}$ ((18F)fluoranylaluminum(2+)), and biomolecules (for example proteins, peptides, carbohydrates, phospholipids, fatty acids, nucleosides, deoxynucleosides, nucleotides and deoxynucleotides; preferred proteins include antibodies, antibody fragments, nanobodies and affibodies) labeled with the aforementioned coordination complexes. Labeled biomolecules of this kind are generally conjugated with the coordination complex by means of a covalent bond.

The scope of the invention also includes a method of labelling a compound of Formula (I) or (II) as defined above with $^{18}F$, comprising contacting said compound with $[AlF]^{2+}$ ((18F)fluoranylaluminum(2+)) in an aqueous medium.

According to one preferred embodiment, the pH of the aqueous medium is comprised between 3.5 and 6.5, preferably between 4.5 and 5.5, and/or the temperature of the aqueous medium is comprised between 200 and 80° C., preferably between 300 and 40° C., more preferably is of about 37° C.

According to one preferred embodiment, the compound of formula (I) or (II) is conjugated with a biomolecule as defined above.

The coordination complexes and the labeled biomolecules which fall within the scope of the present invention are suitable for use in imaging methods for diagnosing diseases, for example tumors, by means of positron emission tomography (PET). This diagnostic application falls within the scope of the present invention.

The chelating compounds of the invention include two amines, two carboxylates and one phenolate among the donor groups. The presence of phenolate groups which can be functionalized in an equal position with chemical groups that allow efficient conjugation with biomolecules and/or the presence of secondary amines which can also be used to insert groups suitable for bioconjugation make these chelating agents particularly suitable for bioimaging applications. As a result of these features, the chelating agents can advantageously allow a kit to be developed for radiolabelling heat-sensitive biomolecules with fluorine-18 at ambient temperature.

Proceeding from the structure of 2- (3- and 4-) aminomethyl piperidine containing a secondary heterocyclic amine and a primary exocyclic amine, the inventors alternated carboxylate and phenolate donor groups so as to obtain the pentadentate chelating agents of the invention. Moreover, the same donor groups (two carboxylates and one phenolate) were inserted onto the structure of trans-1,2-cyclohexane diamine, which is already known in the literature for forming stable chelating agents for numerous metal ions, also including [AlF]$^{2+}$. Finally, the further rigidification of the cycles (both of piperidine and of cyclohexane diamine) proceeding from 2-aminomethyl-azabicyclo[2.2.1]heptane (or [3.2.1]octane) or from trans-bicyclo[2.2.1]heptane-2,3-diamine guaranteed a further increase in kinetic inertia of the radioactive tracer.

With regard to bicyclic chelating agents, the synthesis of the pentadentate chelating agents follows published procedures for the synthesis of diamine precursors. In particular, for the synthesis of 3-aminomethyl-2-azabicyclo[2.2.1]heptane, the following publication (Gujarro et al. *J. Org. Chem.* 1998, 63, 2530-2535) describes the synthesis of a hydroxymethyl derivate which can be easily transformed into aminomethyl and then subsequently alkylated to obtain the desired rigid chelating agents. However, Hatano et al., *J. Chem. Soc. Perkin Trans.* 2, 1994, 579-584 describes the synthesis of trans-bicyclo[2.2.1]heptane-2,3-diamine which can then be used as a starting point for the synthesis of rigid derivates of the CDDA-HB type.

The reactions for labelling with [AlF-18]$^{2+}$ were carried out at various pH (between 4 and 6.5) and at various temperatures (25, 37 and 80°). The preparation of [AlF-18]$^{2+}$ and the subsequent labelling with the chelating agents covered by the present patent were carried out according to the procedure cited by Bormans and colleagues (*Nature Prot.* 2018, 13, 2330-2347). The labeled products were purified using Sep-Pak Alumina N Plus Light cartridges and eluted with a 0.9% NaCl solution. All of the products were analyzed by means of radio-TLC and radio-HPLC and the stability of the tracers was studied at 10, 30, 60, 120 and 240 minutes by means of incubation in three different solutions: human serum, PBS, EDTA 5 mM and 0.9% NaCl solutions.

A radiolabelling efficiency of between 54 and 79% at pH 5 and ambient temperature (54% 2-AMPDA-HB, 69% 2-AMPDA-NHB, and 79% 2-AMPTA) was obtained for all of the chelating agents. Moreover, the chelating agent 2-AMPTA achieves 91.5% radiolabelling yield at pH 4.5, whereas the ligand 2-AMPDA-HB has a radiolabelling yield of 65% at pH 6 and of 43.5% at pH 6.5.

A similar result was obtained at 37° C. and at pH 5, where the radiolabelling efficiency is 60% for 2-AMPDA-HB, 68% for 2-AMPDA-HB, and 75% for 2-AMPTA.

The labelling efficiency at ambient temperature is greater than that obtained using the chelating agents cited in the literature (35-55% for RESCA1, cf. *Nature Prot.* 2018, 13, 2330-2347, page 2333 and the abstract).

The increased radiolabelling efficiency of the compounds of the present invention is also highlighted by comparison with the compound L26 that is described in the patent application WO/2016/065435 cited on page 2331 of *Nature Prot.* 2018, 13, 2330-2347.

The chelating agent 2-AMPTA achieves 91.5% radiolabelling yield at pH 4.5, whereas the ligand 2-AMPDA-HB has a radiolabelling yield of 65% at pH 6 and of 43.5% at pH 6.5. The chelating agent L26 has a radiolabelling yield of 86% at pH 5, whereas at pH 6 and 6.5 its radiolabelling yield decreases to 55% and 25%, respectively, which are much lower than that observed for 2-AMPDA-HB.

Consequently, the labelling yield of the AMP derivates of the present invention is higher, above all at a pH between 6 and 6.5, which thus also indicates a possible use with pH-sensitive substrates (in addition to temperature-sensitive substrates). Moreover, with regard to 2-AMPTA, yields greater than 90% are achieved at pH 4.5, which are not achieved for the chelating agent L26.

An additional advantage is the stability in human serum detected for the compounds of the present invention. An increased stability in human serum was measured for the chelating agent 2-AMPDA-HB, with 90% of AlF-18 still complexed after 120 minutes, whereas the complexed percentage was 55% for the chelating agent 2-AMPTA. Moreover, the stability of the AlF-18 complexes after 240 minutes in human serum was found to be, respectively, 87% for the chelating agent 2-AMPDA-HB and 33% for the chelating agent 2-AMPTA.

An additional advantage of the compounds of the present invention is evidenced by the biodistribution data of [Al$^{18}$F(2-AMPDA-HB)]$^-$ measured in selected organs 2 hours after injection onto healthy nude mice. The accumulated activity is provided as a percentage of the injected dose per gram (% ID/g±SD) (n=6). For [Al$^{18}$F(2-AMPDA-HB)]$^-$, the percentages of injected dose accumulated in the organs was much lower than that measured for L26. In particular, an accumulation of [Al$^{18}$F(2-AMPDA-HB)]$^-$ of 1.63% ID±0.73 at 120 min was observed in the bones, contrary to 1.90% ID±0.30 at 60 min for L26. Considering that accumulation in the bones is a clear indication of the release of Al$^{18}$F from the complex, these data demonstrate an advantage of the present invention, since, given the same period of time, the accumulation of [Al$^{18}$F(2-AMPDA-HB)]$^-$ will be much lower than the accumulation of L26. These results are also very promising in relation to other in vivo studies cited in the literature (for example in F. Cleeren et al, Bioconjugate Chem. 2016, 27, 790-798], which show an accumulation in the bones of free $\{Al^{18}F\}^{2+}$ that is equal to 83% ID±10.65 and $\{Al^{18}F\}^{2+}$ ligands of 2.5% ID±0.64 at 60 min p.i.

The aforementioned comparative data relating to the radiolabelling yield, stability in human serum and biodistribution are relative to compounds covered by Formula (I). Nevertheless, considering the similar number and type of donor atoms (two amine nitrogen atoms and three oxygens, two carboxylates and one phenolate) and the similar spatial arrangement thereof, it is conceivable that the complexation of Al$^{18}$F and therefore the labelling yield, the stability in serum and the biodistribution are similar for compounds of Formula (II).

The following experimental part illustrates the procedures for synthesizing rigidified pentadentate chelating agents which fall within the scope of the present invention. This experimental part is provided merely by way of non-limiting illustration of the scope of the invention as defined in the appended claims.

EXPERIMENTAL PART

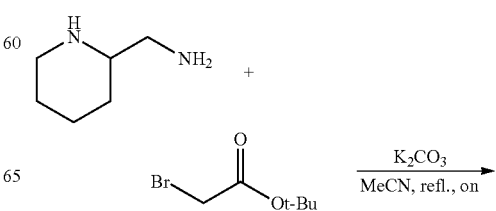

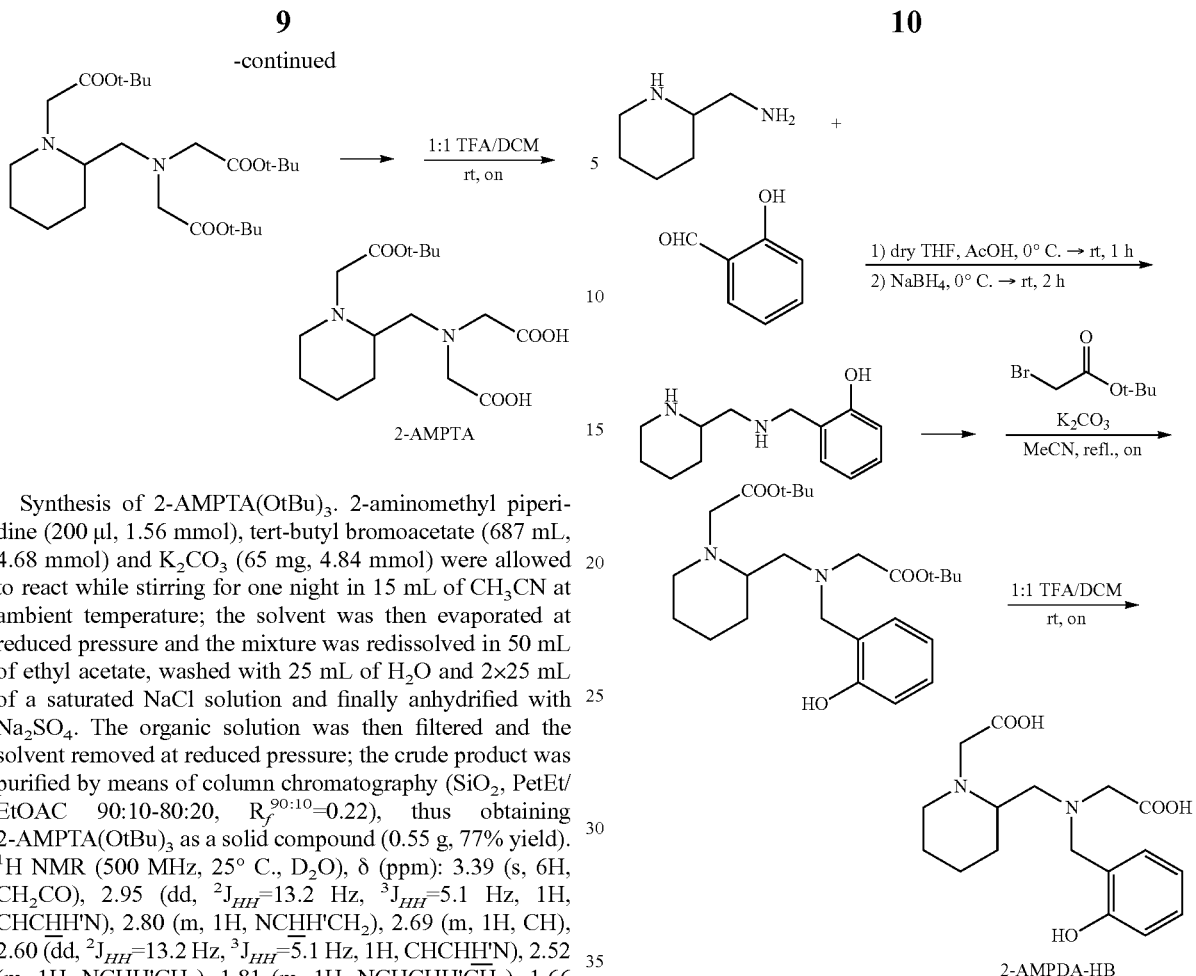

2-AMPTA

Synthesis of 2-AMPTA(OtBu)$_3$. 2-aminomethyl piperidine (200 µL, 1.56 mmol), tert-butyl bromoacetate (687 mL, 4.68 mmol) and K$_2$CO$_3$ (65 mg, 4.84 mmol) were allowed to react while stirring for one night in 15 mL of CH$_3$CN at ambient temperature; the solvent was then evaporated at reduced pressure and the mixture was redissolved in 50 mL of ethyl acetate, washed with 25 mL of H$_2$O and 2×25 mL of a saturated NaCl solution and finally anhydrified with Na$_2$SO$_4$. The organic solution was then filtered and the solvent removed at reduced pressure; the crude product was purified by means of column chromatography (SiO$_2$, PetEt/EtOAC 90:10-80:20, R$_f^{90:10}$=0.22), thus obtaining 2-AMPTA(OtBu)$_3$ as a solid compound (0.55 g, 77% yield). $^1$H NMR (500 MHz, 25° C., D$_2$O), δ (ppm): 3.39 (s, 6H, CH$_2$CO), 2.95 (dd, $^2J_{HH}$=13.2 Hz, $^3J_{HH}$=5.1 Hz, 1H, CHCHH'N), 2.80 (m, 1H, NCHH'CH$_2$), 2.69 (m, 1H, CH), 2.60 (dd, $^2J_{HH}$=13.2 Hz, $^3J_{HH}$=5.1 Hz, 1H, CHCHH'N), 2.52 (m, 1H, NCHH'CH$_2$), 1.81 (m, 1H, NCHCH'CH$_2$), 1.66 (m, 1H, NCH$_2$CHH'), 1.54 (m, 2H, NCHCH$_2$CH$_2$), 1.27 (m, 2H, NCH$_2$CHH'+NCHCHH'CH$_2$). $^{13}$C NMR (125 MHz, 25° C., D$_2$O), δ (ppm): 170.6 (CO), 80.8 (C$^{tBu}$), 57.6 (CH), 57.5 (NCHCH$_2$N), 56.4 (CH$_2$CO), 53.4 (NCH$_2$CH$_2$), 30.5 (NCHCH$_2$CH$_2$), 28.1 (CH$_3$), 25.5 (NCHCH$_2$CH$_2$), 23.6 (NCH$_2$CH$_2$). ESI$^+$ MS: m/z 457.5 [M+H$^+$], calc. for [C$_{24}$H$_{45}$N$_2$O$_6$]$^+$=457.33 g/mol.

Synthesis of 2-AMPTA. 2-AMPTA(OtBu)$_3$ (3.1 g, 0.69 mmol) was dissolved in a 1:1 mixture of TFA and CH$_2$Cl$_2$ (4 mL) and reacted while stirring for 5 hours at ambient temperature. After removing the solvent at reduced pressure, the species was dissolved in CH$_3$CN (1 mL) and precipitated in diethyl ether. The solid was centrifuged (4000 rpm, 15 min) and washed/centrifuged 3 times with diethyl ether, thereby obtaining the white solid 2-AMPTA (0.18 g, 92% yield). $^1$H NMR (500 MHz, 25° C., D$_2$O), δ (ppm): 7.93 (m, 2H, CHCHCNO$_2$+CCHCNO$_2$), 6.88 (d, $^2J_{HH}$=8.8 Hz, 1H, CHCOH), 3.90 (s, 2H, NCH$_2$Ar), 3.71 (m, 3H, NCH+NCHCH$_2$N), 3.51 (m, 5H, NCHCH$_2$N+NCH$_2$CO), 3.32 (m, 1H, NCH$_2$CH$_2$), 3.09 (m, 1H, NCH$_2$CH$_2$), 2.00 (m, 1H, NCH$_2$CH$_2$), 1.9-1.7 (m, 4H, NCHCH$_2$CH$_2$+NCH$_2$CH$_2$), 1.57 (m, 1H, NCHCH$_2$CH$_2$). $^{13}$C NMR (125 MHz, 25° C., D$_2$O), δ (ppm): 173.2 (COOH), 161.8 (COH), 141.0 (CNO$_2$), 128.8 (CCHCNO$_2$), 127.0 (NCH$_2$C), 125.8 (CHCHCNO$_2$), 116.4 (CHCOH), 66.7 (NCH$_2$CO), 60.6 (NCH), 51.8 (NCH$_2$CH$_2$), 39.5 (NCHCH$_2$N), 30.8 (NCH$_2$Ar), 25.1 (NCH$_2$CH$_2$), 20.3 (NCHCH$_2$CH$_2$+NCHCH$_2$CH$_2$). ESI$^+$ MS: m/z 289.4 [M+H$^+$], calc. for [C$_{12}$H$_{21}$N$_2$O$_6$]$^+$=289.14 g/mol. ESI$^+$ MS: m/z. 289.2 (M+H$^+$); calc. for [C$_{12}$H$_{21}$N$_2$O$_6$]$^+$=289.14 g/mol.

Synthesis of 2-(N-(o-hydroxybenzyl)aminomethyl) piperidine. 2-aminomethyl piperidine (100 mg, 0.88 mmol) was dissolved in anhydrous THF (5 mL). A drop of acetic acid and then salicylaldehyde (0.094 mL, 0.88 mmol) were subsequently added at 0° C. and the yellow mixture was allowed to react while stirring for 1 hour at ambient temperature. NaBH$_4$ (333 mg, 8.80 mmol) was then added in portions at 0° C. and the suspension stirred at rt for a further 2 hours. H$_2$O (5 mL) was then added and stirred for another 30 min at rt. 10 mL of AcOEt was then added to the mixture and the organic phase was washed with 25 mL of H$_2$O and 2×25 mL of a saturated NaCl solution, anhydrified with Na$_2$SO$_4$ and filtered. Finally, the solvent was evaporated, thus obtaining N-(o-hydroxybenzyl)-2-aminomethyl piperidine (193 mg) which was used without further purification. ESI+ MS: m/z. 221.2 (M+H$^+$); calc. for [C$_{13}$H$_{21}$N$_2$O]$^+$=221.32 g/mol.

Synthesis of 2-AMPDA-HB(OtBu)$_2$. 2-(N-o-hydroxybenzyl-aminomethyl) piperidine (193 mg, 0.88 mmol, theoretical), tert-butyl bromoacetate (0.258 mL, 1.76 mmol), K$_2$CO$_3$ (486 mg, 1.88 mmol) in CH$_3$CN (10 mL) were reacted for 2 hours while stirring at ambient temperature. After removing the solvent at reduced pressure, the product was redissolved in AcOEt (10 mL) and washed with 5 mL of H$_2$O and 2×5 mL of a saturated NaCl solution. The organic phase was then anhydrified with Na$_2$SO$_4$, filtered and the solvent removed in the rotavapor. The crude product was purified by means of column chromatography (SiO$_2$, PetEt/EtOAc 90:10>70:30, R$_f$(80:20)=0.17), thus obtaining 2-AMPDA-HB(OtBu)$_2$ (165 mg, 42%). $^1$H NMR (500

MHz, 25° C., MeOD), δ (ppm): 7.17 (t, $^3J_{HH}$=7.2 Hz, 1H, CHCHCOH), 6.95 (d, $^3J_{HH}$=7.1 Hz, 1H, CHCCH$_2$), 6.83 (d, $^3J_{HH}$=8.0 Hz, 1H, CHCOH), 6.76 (t, $^3J_{HH}$=7.4 Hz, 1H, CHCHCCH$_2$), 3.90 (s, 2H, NCH$_2$Ar), 3.71 (m, 3H, NCH+NCHCH$_2$N), 3.51 (m, 5H, NCHCH$_2$N+NCH$_2$CO), 3.32 (m, 1H, NCH$_2$CH$_2$), 3.09 (m, 1H, NCH$_2$CH$_2$), 2.08 (m, 1H, NCH$_2$CH$_2$), 1.9-1.7 (m, 4H, NCHCH$_2$CH$_2$+NCH$_2$CH$_2$), 1.58 (m, 1H, NCHCH$_2$CH$_2$), 1.48 (s, 9H, 3×CH$_3$), 1.46 (s, 9H, 3×CH$_3$). $^{13}$C NMR (125 MHz, 25° C., MeOD), δ (ppm): 170.3 (CO), 157.5 (COH), 129.5 (CHCCH$_2$), 129.2 (CHCHCOH), 122.0 (CCH$_2$), 119.2 (CHCHCCH$_2$), 116.4 (CHCOH), 82.3 (C$^{tBu}$), 59.4 (NCH$_2$CO), 58.8 (NCH$_2$Ar), 60.6 (NCH), 51.8 (NCH$_2$CH$_2$), 39.5 (NCHCH$_2$N), 28.2 (CH$_3$), 25.1 (NCH$_2$CH$_2$), 20.3 (NCHCH$_2$CH$_2$+NCHCH$_2$CH$_2$). ESI$^+$ MS: m/z. 449.4 (M+H$^+$); calc. for [C$_{25}$H$_{41}$N$_2$O$_5$]$^+$=449.30 g/mol.

Synthesis of 2-AMPDA-HB. 2-AMPDA-HB(OtBu)$_2$ (88 mg, 0.20 mmol) was reacted with TFA (2 mL), CH$_2$Cl$_2$ (2 mL) and a drop of triisopropylsilane for 15 hours while stirring at ambient temperature. The solvents were then evaporated at reduced pressure and the residue was dissolved in CH$_3$CN (1 mL) and precipitated in diethyl ether. The solid was centrifuged and washed 3 times with diethyl ether, thus obtaining 2-AMPDA-HB (61 mg, 90%). $^1$H NMR (500 MHz, 25° C., D$_2$O), δ (ppm): 7.34 (m, 2H, CHCHCNO$_2$+CCHCNO$_2$), 6.88 (d, $^2J_{HH}$=8.8 Hz, 1H, CHCOH), 3.90 (s, 2H, NCH$_2$Ar), 3.71 (m, 3H, NCH+NCHCH$_2$N), 3.51 (m, 5H, NCHCH$_2$N+NCH$_2$CO), 3.32 (m, 1H, NCH$_2$CH$_2$), 3.09 (m, 1H, NCH$_2$CH$_2$), 2.08 (m, 1H, NCH$_2$CH$_2$), 1.9-1.7 (m, 4H, NCHCH$_2$CH$_2$+NCH$_2$CH$_2$), 1.58 (m, 1H, NCHCH$_2$CH$_2$). $^{13}$C NMR (125 MHz, 25° C., D$_2$O), δ (ppm): 173.2 (COOH), 161.8 (COH), 141.0 (CNO$_2$), 128.8 (CCHCNO$_2$), 127.0 (NCH$_2$C), 125.8 (CHCHCNO$_2$), 116.4 (CHCOH), 66.7 (NCH$_2$CO), 60.6 (NCH), 51.8 (NCH$_2$CH$_2$), 39.5 (NCHCH$_2$N), 30.8 (NCH$_2$Ar), 25.1 (NCH$_2$CH$_2$), 20.3 (NCHCH$_2$CH$_2$+NCHCH$_2$CH$_2$). ESI$^+$ MS: m/z 337.4 [M+H$^+$], calc. for [C$_{17}$H$_{25}$N$_2$O$_5$]$^+$=337.18 g/mol.

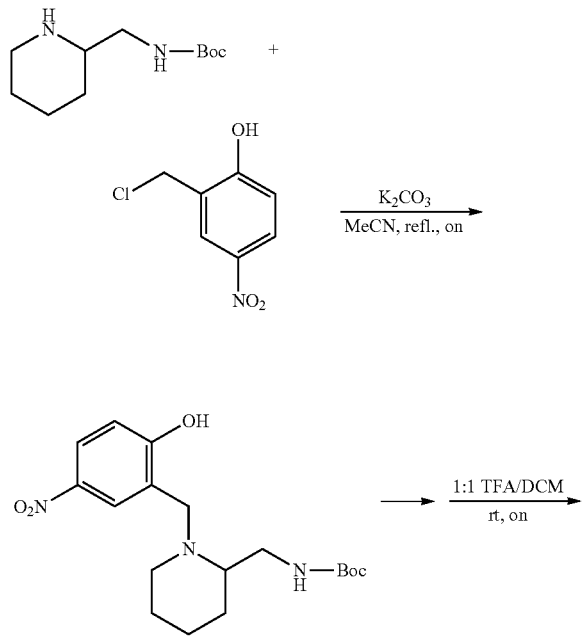

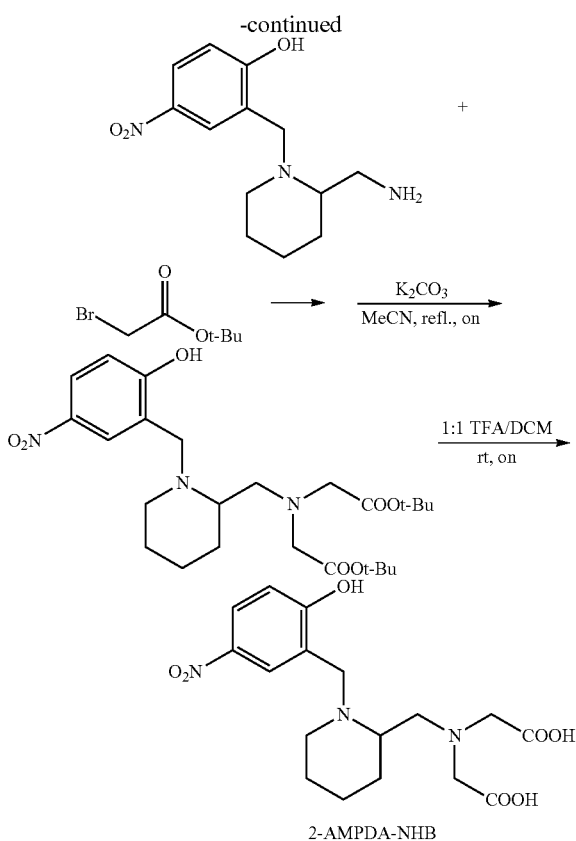

2-Boc-aminomethyl)-N-(2-hydroxybenzyl-4-nitrophenylmethyl) piperidine. 2-(Boc-aminomethyl) piperidine (322 mg, 1.50 mmol) was dissolved in DMF (10 mL). K$_2$CO$_3$ (415 mg, 3.00 mmol) was then added, followed by 2-chloromethyl-4-nitrophenol (563 mg, 3.00 mmol), and the mixture was stirred under reflux overnight. After removing the solvent at reduced pressure, the product was redissolved in AcOEt (40 mL) and washed with 2×50 mL of H$_2$O and 50 mL of a saturated NaCl solution. The organic phase was then anhydrified with Na$_2$SO$_4$, filtered and the solvent removed in the rotavapor. The crude product was purified by means of column chromatography (SiO$_2$, cyclohexane/acetone 95:5>80:20, R$_f$(90:10)=0.34) to obtain 2-Boc-aminomethyl)-N-(2-hydroxy-4-nitrophenylmethyl) piperidine as a white solid (262 mg, 48%).

$^1$H NMR (500 MHz, 25° C., CDCl$_3$), δ (ppm): 7.94 (d, $^2J_{HH}$=8.9 Hz, 1H, CHCHCNO$_2$), 7.82 (s, 1H, CCHCNO$_2$), 6.70 (d, $^2J_{HH}$=8.9 Hz, 1H, CHCOH), 4.37 (d, $^2J_{HH}$=12.1 Hz, 1H, NCH$_2$Ar), 3.61 (d, $^2J_{HH}$=12.1 Hz, 1H, NCH$_2$Ar), 3.40 (m, 1H, CH$_2$NH), 3.33 (m, 1H, CH$_2$NH), 2.85 (m, 1H, NCH), 2.60 (m, 1H, NCH$_2$CH$_2$), 2.27 (m, 1H, NCH$_2$CH$_2$), 1.69 (m, 1H, NCHCH$_2$CH$_2$), 1.68 (m, 1H, NCHCH$_2$CH$_2$), 1.55 (m, 1H, NCHCH$_2$CH$_2$), 1.49 (m, 2H, NCHCH$_2$CH$_2$+NCH$_2$CH$_2$), 1.39 (m, 1H, NCH$_2$CH$_2$), 1.32 (s, 9H, CH$_3$). $^{13}$C NMR (125 MHz, 25° C., CDCl$_3$), δ (ppm): 165.2 (COH), 156.0 (COO), 139.5 (CNO$_2$), 125.0 (CCHCNO$_2$), 124.6 (NCH$_2$C), 121.5 (CHCHCNO$_2$), 116.3 (CHCOH), 79.5 (C$^{tBu}$), 60.5 (NCH), 60.3 (NCH$_2$CH$_2$), 56.3 (NCH$_2$Ar), 50.8 (CH$_2$NH), 40.9 (NCHCH$_2$CH$_2$), 28.2 (CH$_3$$^{tBu}$), 24.1 (NCH$_2$CH$_2$), 20.9 (NCHCH$_2$CH$_2$). ESI$^+$ MS: m/z 366.6 [M+H$^+$], calc. for [C$_{18}$H$_{28}$N$_3$O$_5$]$^+$=366.20 g/mol.

2-aminomethyl-N-(2-hydroxy-4-nitrophenylmethyl) piperidine. 2-Boc-aminomethyl)-N-(2-hydroxy-4-nitrophenylmethyl) piperidine (235 mg, 0.64 mmol) was dissolved in DCM (5 mL). TFA (5 mL) was added and the mixture was stirred at rt for 3 hours. The solvents were then evaporated at reduced pressure and the residue redissolved in TFA (1 mL) and precipitated while adding Et$_2$O (10 mL). The suspension was then centrifuged (4000 rpm, 15 min, 10° C.) and the precipitate washed/centrifuged with Et$_2$O (3×10 mL). The product was obtained as a salt of trifluoroacetate (216 mg, 89%).

$^1$H NMR (500 MHz, 25° C., MeOD), δ (ppm): 8.31 (s, 1H, CCHCNO$_2$), 8.17 (d, $^2J_{HH}$=9.0 Hz, 1H, CHCHCNO$_2$), 7.02 (d, $^2J_{HH}$=8.9 Hz, 1H, CHCOH), 4.54 (d, $^2J_{HH}$=13.2 Hz, 1H, NCH$_2$Ar), 4.30 (d, $^2J_{HH}$=13.2 Hz, 1H, NCH$_2$Ar), 3.72 (m, 1H, CH$_2$NH), 3.68 (m, 1H, NCH), 3.46 (m, 1H, CH$_2$NH), 3.37 (m, 1H, NCH$_2$CH$_2$), 3.07 (m, 1H, NCH$_2$CH$_2$), 2.12 (m, 1H, NCH$_2$CH$_2$), 1.86-1.83 (m, 4H, NCHCH$_2$CH$_2$+NCH$_2$CH$_2$), 1.62 (m, 1H, NCHCH$_2$CH$_2$). $^{13}$C NMR (125 MHz, 25° C., CDCl$_3$), δ (ppm): 162.6 (COH), 140.4 (CNO$_2$), 128.8 (CCHCNO$_2$+CCHCNO$_2$), 127.8 (CHCHCNO$_2$), 116.1 (CHCOH), 60.5 (NCH), 51.2 (NCH$_2$CH$_2$), 48.7 (NCH$_2$Ar), 38.9 (CH$_2$NH$_2$), 24.8 (NCH$_2$CH$_2$), 20.3 (NCHCH$_2$CH$_2$+NCHCH$_2$CH$_2$). ESI$^+$ MS: m/z 266.2 [M+H$^+$], calc. for [C$_{13}$H$_{20}$N$_3$O$_3$]$^+$=266.15 g/mol.

2-AMPDA-NHB(OtBu)$_2$. 2-aminomethyl-N-(2-hydroxy-4-nitrophenylmethyl) piperidine (216 mg, 0.57 mmol) was dissolved in DMF (2 mL). K$_2$CO$_3$ (157 mg, 1.14 mmol) was added, followed by t-butyl bromoacetate (0.167 mL, 1.14 mmol), and the mixture was stirred at rt for 18 hours. After removing the solvent at reduced pressure, the product was redissolved in AcOEt (10 mL) and washed with 2×5 mL of H$_2$O and 5 mL of a saturated NaCl solution. The organic phase was then anhydrified with Na$_2$SO$_4$, filtered and the solvent removed in the rotavapor. The crude product was purified by means of flash chromatography (SiO$_2$, PetEt/EtOAc 60:40→20:80, R$_f^{30:70}$=0.24), thus obtaining the product 2-AMPDA-NHB(OtBu)$_2$ as a yellow solid (194 mg, 69%).

$^1$H NMR (500 MHz, 25° C., CDCl$_3$), δ (ppm): 8.31 (d, $^2J_{HH}$=8.9 Hz, 1H, CHCHCNO$_2$), 7.85 (s, 1H, CCHCNO$_2$), 6.75 (d, $^2J_{HH}$=8.9 Hz, 1H, CHCOH), 3.93 (d, $^2J_{HH}$=12.1 Hz, 1H, NCH$_2$Ar), 3.79 (d, $^2J_{HH}$=12.1 Hz, 1H, NCH$_2$Ar), 3.5-3.3 (m, 5H, NCH+NCH$_2$CO), 3.30 (m, 1H, CHCH$_2$N), 3.08 (m, 1H, NCH$_2$CH$_2$), 2.88 (m, 1H, CHCH$_2$N), 2.75 (m, 1H, NCH$_2$CH$_2$), 2.04 (m, 1H, NCH$_2$CH$_2$), 1.8-1.7 (m, 4H, NCHCH$_2$CH$_2$+NCH$_2$CH$_2$), 1.63 (m, 1H, NCHCH$_2$CH$_2$). 1.42 (s, 18H, CH$_3$). $^{13}$C NMR (125 MHz, 25° C., CDCl$_3$), δ (ppm): 169.8 (COO), 163.8 (COH), 140.6 (CNO$_2$), 129.4 (CCHCNO$_2$), 127.3 (NCH$_2$C), 125.3 (CHCHCNO$_2$), 118.0 (CHCOH), 83.0 (C$^{tBu}$), 60.6 (NCH), 57.9 (NCH$_2$CO), 56.1 (NCHCH$_2$N), 50.6 (NCH$_2$CH$_2$), 39.9 (NCH$_2$Ar), 28.8 (CH$_3^{tBu}$), 26.2 (NCH$_2$CH$_2$), 22.4 (NCHCH$_2$CH$_2$), 21.4 (NCHCH$_2$CH$_2$). ESI$^+$ MS: m/z 494.4 [M+H$^+$], calc. for [C$_{25}$H$_{40}$N$_3$O$_7$]$^+$=494.29 g/mol.

2-AMPDA-NHB. 2-AMPDA-NHB(OtBu)$_2$ (27 mg, 0.055 mmol) was reacted with TFA (2 mL), CH$_2$Cl$_2$ (2 mL) and a drop of triisopropylsilane for 15 hours while stirring at ambient temperature. The solvents were then evaporated at reduced pressure and the residue was dissolved in concentrated HCl (5 mL) and, after stirring for 30 min, the solvent was removed in the rotavapor. The residue was then redissolved with TFA (1 mL) and precipitated in diethyl ether (10 mL). The solid was centrifuged and washed 3 times with diethyl ether, thus obtaining 2-AMPDA-HB hydrochloride (14 mg, 61%) after drying under vacuum.

$^1$H NMR (500 MHz, 25° C., D$_2$O), δ (ppm): 7.93 (m, 2H, CHCHCNO$_2$+CCHCNO$_2$), 6.88 (d, $^2J_{HH}$=8.8 Hz, 1H, CHCOH), 3.90 (s, 2H, NCH$_2$Ar), 3.71 (m, 3H, NCH+NCHCH$_2$N), 3.51 (m, 5H, NCHCH$_2$N+NCH$_2$CO), 3.32 (m, 1H, NCH$_2$CH$_2$), 3.09 (m, 1H, NCH$_2$CH$_2$), 2.08 (m, 1H, NCH$_2$CH$_2$), 1.9-1.7 (m, 4H, NCHCH$_2$CH$_2$+NCH$_2$CH$_2$), 1.58 (m, 1H, NCHCH$_2$CH$_2$). $^{13}$C NMR (125 MHz, 25° C., D$_2$O), δ (ppm): 173.2 (COOH), 161.8 (COH), 141.0 (CNO$_2$), 128.8 (CCHCNO$_2$), 127.0 (NCH$_2$C), 125.8 (CHCHCNO$_2$), 116.4 (CHCOH), 66.7 (NCH$_2$CO), 60.6 (NCH), 51.8 (NCH$_2$CH$_2$), 39.5 (NCHCH$_2$N), 30.8 (NCH$_2$Ar), 25.1 (NCH$_2$CH$_2$), 20.3 (NCHCH$_2$CH$_2$+NCHCH$_2$CH$_2$). ESI$^+$ MS: m/z 382.2 [M+H$^+$], calc. for [C$_{17}$H$_{24}$N$_3$O$_7$]$^+$=382.16 g/mol.

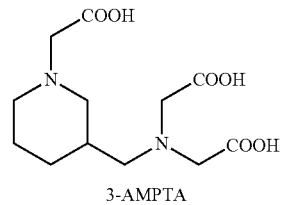 [SMILES: O=C(O)CN1CCCC(CN(CC(=O)O)CC(=O)O)C1]

3-AMPTA

Synthesis of 3-AMPTA(OtBu)$_3$. 3-aminomethyl piperidine (200 µl, 1.56 mmol), tert-butyl bromoacetate (687 ml, 4.68 mmol) and K$_2$CO$_3$ (65 mg, 4.84 mmol) were allowed to react while stirring for one night in 15 mL of CH$_3$CN at ambient temperature; the solvent was then evaporated at reduced pressure and the mixture was redissolved in 50 mL of CHCl$_3$, washed with 3×25 mL of water and finally anhydrified with Na$_2$SO$_4$. The organic solution was filtered and the solvent removed at reduced pressure; the crude product was purified by means of column chromatography (SiO$_2$, acetone/hexane 5:95>20:80), thus obtaining 3-AMPTA(OtBu)$_3$ as a solid compound (0.51 g, 71.5% yield), ESI$^+$ MS, m/z: 457.4 (M+H$^+$); calc. for [C$_{24}$H$_{45}$N$_2$O$_6$]$^+$=457.33 g/mol. $^1$H NMR (D$_2$O, 500 MHz), δ(ppm): 3.96 (s, 4H, 2×CH$_2$), 3.84 (s, 2H, CH$_2$), 3.67 (d, 2H, CHCH$_2$N), 3.26 (m, 2H, CH$_2^{pip}$), 3.04 (m, 2H, CH$_2^{pip}$), 2.14 (m, 3H, CH+ CH$_2^{pip}$), 1.64 (m, 2H, CH$_2^{pip}$), 1.18 (s, 27H, CH$_3$). $^{13}$C NMR (D$_2$O, 500 MHz) δ(ppm): 170.3 (CO), 169.5 (CO), 66.7 (C), 61.6 (CH$_2$), 58.3 (CH$_2$), 58.1 (CH$_2$), 53.5 (CH$_2$), 30.3 (CH$_2$), 29.8 (CH$_2$), 27.6 (CH$_2$), 14.8 (CH$_3$).

Synthesis of 3-AMPTA. 3-AMPTA(OtBu)$_3$ (74 mg) was dissolved in a 1:1 mixture of TFA and CH$_2$Cl$_2$ (4 mL) and reacted while stirring for 5 hours at ambient temperature. After removing the solvent at reduced pressure, the species was dissolved in CH$_3$CN (1 mL) and precipitated in diethyl ether. The solid was centrifuged and washed 3 times with diethyl ether, thus obtaining the white solid 3-AMPTA. The final quantity is equal to 49 mg and the yield is quantitative.

$^1$H NMR (500 MHz, 25° C., D$_2$O), δ (ppm): 3.93 (s, 4H, 2×CH$_2$), 3.82 (s, 2H, CH$_2$), 3.54 (d, 2H, CHCH$_2$N), 2.46 (m, 2H, CH$_2^{pip}$), 2.42 (m, 2H, CH$_2^{pip}$), 1.73 (m, 1H, CH), 1.72 (m, 2H, CH$_2^{pip}$), 1.68 (m, 2H, CH$_2^{pip}$). $^{13}$C NMR (125 MHz, 25° C., D$_2$O), δ (ppm): 173.9 (CO), 173.1 (CO), 63.2 (CH$_2$), 59.9 (2×CH$_2$), 58.2 (CH$_2$), 54.5 (CH$_2$), 30.7 (CH$_2$), 30.1 (CH$_2$), 28.6 (CH$_2$), 26.7 (CH). ESI$^+$ MS: m/z. 289.2 (M+H$^+$); calc. for [C$_{12}$H$_{21}$N$_2$O$_6$]$^+$=289.14 g/mol.

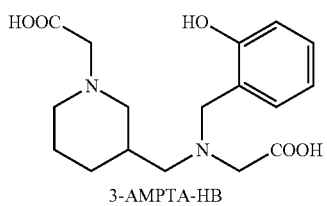 [SMILES: O=C(O)CN1CCCC(CN(CC(=O)O)Cc2ccccc2O)C1]

3-AMPTA-HB

Synthesis of 3-(N-o-hydroxybenzyl-aminomethyl) piperidine. 3-aminomethyl piperidine (200 mL, 1.57 mmol) and salicylaldehyde (104 mL, 1.57 mmol) in $CH_3OH$ (5 ml) were reacted while stirring for 3 hours at ambient temperature, and then $NaBH_4$ (175 mg, 4.71 mmol) was added in an ice bath and the reaction continued while stirring for another 3 hours. The solvent was then evaporated at reduced pressure. The mixture was dissolved in 25 mL of AcOEt and washed with 3×10 mL of $H_2O$. The organic solution was then anhydrified with $Na_2SO_4$, filtered through a pleated filter and the solvent was evaporated, thus obtaining N-(o-hydroxybenzyl)-3-aminomethyl piperidine (107 mg, 31%). $^1$H NMR (500 MHz, 25° C., MeOD), δ (ppm): 7.21 (t, $^3J_{HH}$=7.6 Hz, 1H, C$\underline{H}$CHCOH), 7.13 (d, $^3J_{HH}$=7.4 Hz, 1H, C$\underline{H}$CCH$_2$), 6.85 (d, $^3J_{HH}$=8.1 Hz, 1H, C$\underline{H}$COH), 6.82 (t, $^3J_{HH}$=7.4 Hz, 1H, C$\underline{H}$CHCH$_2$), 4.10 (m, 2H, CH$_2$Ar), 3.51 (m, 1H, NHCHH'$^{Pi}$CH), 3.26 (m, 1H, NHC$\underline{H}$H'CH$_2$), 2.84 (m, 2H, NHC$\underline{H}_2$CH), 2.77 (m, 1H, NHCHH'CH$_2$), 2.61 (m, 1H, NHCHH'$^{Pi}$CH), 2.32 (m, 1H, NHCH$_2$C$\underline{H}$), 1.9-1.8 (m, 3H, NHCH$_2$C$\underline{H}_2$+CHCHH'CH$_2$), 1.21 (m, 1H, CHCH-H'CH$_2$). $^{13}$C NMR (125 MHz, 25° C., MeOD), δ (ppm): 155.9 (COH), 141.0 (CNO$_2$), 131.5 (C$\underline{H}$CHCOH+CHC), 126.9 (C$\underline{CH}_2$), 120.3 (C$\underline{H}$CHC), 115.9 (C$\underline{H}$COH), 49.1 (NHC$\underline{H}_2$CH), 48.3 (NHC$\underline{H}_2$C), 46.3 (NHCH$_2$$^{Pi}$CH), 43.8 (NHC$\underline{H}_2$CH$_2$), 31.2 (NHCH$_2$C$\underline{H}$), 26.5 (CHC$\underline{H}_2$CH$_2$), 21.5 (NHCH$_2$C$\underline{H}_2$). ESI$^+$ MS: m/z 221.1 [M+H$^+$], calc. for [C$_{13}$H$_{21}$N$_2$O]$^+$=221.16 g/mol.

Synthesis of 3-AMPDA-HB(OtBu)$_2$. 3-(N-o-hydroxybenzyl-aminomethyl) piperidine (107 mg, 0.49 mmol), tert-butyl bromoacetate (144 ml, 0.98 mmol) and $K_2CO_3$ (148 mg, 1.07 mmol) in $CH_3CN$ (10 mL) were reacted for 2 hours while stirring at ambient temperature; after removing the solvent at reduced pressure, the crude product was purified by means of column chromatography ($SiO_2$, acetone/hexane 10:90>40-60), thus obtaining 3-AMPDA-HB(OtBu)$_2$ (101 mg, 46%). ESI+ MS: m/z. 449.4 (M+H$^+$). $^1$H NMR (500 MHz, 25° C., MeOD), δ (ppm): 7.17 (t, $^3J_{HH}$=7.2 Hz, 1H, C$\underline{H}$CHCOH), 6.95 (d, $^3J_{HH}$=7.1 Hz, 1H, C$\underline{H}$CCH$_2$), 6.83 (d, $^3J_{HH}$=8.0 Hz, 1H, C$\underline{H}$COH), 6.76 (t, $^3J_{HH}$=7.4 Hz, 1H, C$\underline{H}$CHCCH$_2$), 3.77 (d, $^2J_{HH}$=13.5 Hz, 1H, NC$\underline{H}$H'Ar), 3.68 (d, $^2J_{HH}$=13.5 Hz, 1H, NCH$\underline{H}$'Ar), 3.28 (d, $^2J_{HH}$=13.5 Hz, 1H, NC$\underline{H}$H'CO), 3.19 (d, $^2J_{HH}$=13.5 Hz, 1H, NCH$\underline{H}$'CO), 3.21 (bs, 2H, NCH$_2$CO), 2.97 (m, 2H, NC$\underline{H}_2$$^{Pip}$CH), 2.37 (d, $^3J_{HH}$=7.0 Hz, 2H, NC$\underline{H}_2$CH), 2.03 (m, 1H, CH$^{Pip}$), 1.96 (m, 1H, CH$^{Pip}$), 1.76 (m, 2H, 2×CH$^{Pip}$), 1.68 (m, 1H, CH$^{Pip}$), 1.48 (s, 9H, 3×CH$_3$), 1.46 (s, 9H, 3×CH$_3$), 0.84 (m, 2H, 2×CH$^{Pip}$). $^{13}$C NMR (125 MHz, 25° C., MeOD), δ (ppm): 170.3 (CO), 157.5 (COH), 129.5 (C$\underline{H}$CCH$_2$), 129.2 (C$\underline{H}$CHCOH), 122.0 (C$\underline{CH}_2$), 119.2 (C$\underline{H}$CHCCH$_2$), 116.4 (C$\underline{H}$COH), 82.3 (C$^{tBu}$), 59.4 (NCH$_2$CO), 58.8 (NCH$_2$Ar), 57.4 (NC$\underline{H}_2$CH), 55.6 (NC$\underline{H}_2$CO), 53.4 (CH$_2$$^{Pip}$), 33.6 (CH$_2$$^{Pip}$), 28.2 (CH$_3$+2×CH$_2$$^{Pip}$), 24.5 (CH$_2$$^{Pip}$). ESI$^+$ MS: m/z 449.5 [M+H$^+$], calc. for [C$_{25}$H$_{41}$N$_2$O$_5$]$^+$=449.30 g/mol.

Synthesis of 3-AMPDA-HB. 3-AMPDA-HB(OtBu)$_2$ (101 mg) was reacted with TFA (6 mL) and $CH_2Cl_2$ (6 mL) for 3 hours while stirring at ambient temperature, and the product was then dissolved in $CH_3CN$ (1 mL) and precipitated in diethyl ether. The solid was centrifuged and washed 3 times with diethyl ether, thus obtaining 3-AMPDA-HB (75 mg, 98%). ESI+ MS: m/z. 337.2 (M+H$^+$). $^1$H NMR (D$_2$O, 500 MHz), δ(ppm): 7.34 (t, 1H, CH$^{Ar}$), 7.30 (d, 1H, CH$^{Ar}$), 6.96 (m, 1H, 2×CH$^{Ar}$), 4.44 (m, 2H, CH$_2$), 3.84 (s, 2H, CH$_2$), 3.80 (s, 2H, C$\underline{H}_2$), 3.68 (m, 1H, CH$^{pip}$), 3.57 (m, 1H, CH$^{pip}$), 3.19 (m, 2H, CH$_2$), 2.93 (m, 1H, CH$^{pip}$), 2.74 (m, 1H, CH$_{pip}$), 2.49 (m, 1H, CH$^{pip}$), 2.00 (m, 1H, CH$_2$$^{pip}$), 1.81 (m, 1H, CH$^{pip}$), 1.25 (m, 1H, CH$^{pip}$). $^{13}$C NMR (D$_2$O, 500 MHz) δ(ppm): 170.3 (CO), 169.4 (CO), 156.0 (C$^{Ar}$OH), 133.3 (CH$^{Ar}$), 133.0 (CH$^{Ar}$), 121.6 (CH$^{Ar}$), 116.4 (CH$^{Ar}$), 116.2 (C$^{Ar}$), 66.7 (CH$_2$), 58.4 (CH$_2$), 56.8 (CH$_2$), 55.7 (CH$_2$), 54.3 (CH$_2$), 31.4 (CH), 26.0 (CH$_2$), 22.6 (CH$_2$).

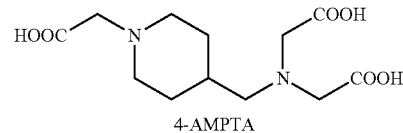 [SMILES: O=C(O)CN1CCC(CN(CC(=O)O)CC(=O)O)CC1]

4-AMPTA

Synthesis of 4-AMPTA(OtBu)$_3$. 4-aminomethyl piperidine (500 mL, 4.17 mmol), tert-butyl bromoacetate (1.895 mL, 12.92 mmol) and $K_2CO_3$ (1.79 g, 12.93 mmol) in $CH_3CN$ (15 ml) were stirred for 5 hours at ambient temperature. After removing the solvent at reduced pressure, the crude product was purified by means of column chromatography ($SiO_2$, acetone/hexane 10:90>30:70), thus obtaining 4-AMPTA tri(OtBu) as a solid compound (1.26 g, 66%). ESI$^+$ MS, m/z: 457.4 (M+H$^+$). $^1$H NMR (CDCl$_3$, 500 MHz), δ(ppm): 3.38 (s, 4H, CH$_2$), 3.13 (s, 2H, CH$_2$), 2.21-2.97 (d, 2H, CH$_2$, cycle), 2.57-2.55 (d, 2H, CH$_2$), 1.67 (s, 2H, CH$_2$, cycle), 1.80-1.77 (d, 2H, CH$_2$, cycle), 1.35-1.30 (m, 3H, CH$_2$—CH). $^{13}$C NMR (CDCl$_3$, 500 MHz), δ(ppm): 171.6 (CO), 81.6 (C(CH$_3$)$_3$), 61.4 (CH$_2$, cycle), 60.9 (NCH$_2$COOt-Bu), 57.4 (N(C$\underline{H}_2$COOt-Bu)$_2$), 54.0 (CH$_2$, —NC$\underline{H}_2$, cycle), 34.9 (CH, cycle), 31.0 (CH$_2$, CH, cycle), 28.9 (CH$_3$, t-Bu).

Synthesis of 4-AMPTA. 4-AMPTA(OtBu)$_3$ (1.26 g) was dissolved in a 1:1 mixture of TFA and CH$_2$Cl$_2$ (60 mL) and stirred for 5 hours at ambient temperature. After removing the solvent at reduced pressure, the residue was dissolved in $CH_3CN$ (1 mL) and precipitated in diethyl ether. The solid was centrifuged and washed 3 times with diethyl ether, thus obtaining the white solid 4-AMPTA. The final quantity is equal to 686 mg and the yield is 86%. ESI+ MS: m/z. 289.2 (M+H$^+$). ESI+ MS: m/z. 289.2 (M+H$^+$). $^1$H NMR (D$_2$O, 500 MHz), δ(ppm): 4.00 (s, 4H, 2×CH$_2$), 3.88 (s, 2H, CH$_2$), 3.68 (d, 2H, CHC$\underline{H}_2$N), 3.28 (m, 2H, CH$_2$$^{pip}$), 3.05 (m, 2H, CH$_2$$^{pip}$), 2.14 (m, 3H, CH+CH$_2$$^{pip}$), 1.64 (m, 2H, CH$_2$$^{pip}$). $^{13}$C NMR (D$_2$O, 500 MHz) δ(ppm): 169.0 (N(CH$_2$COOH)$_2$), 168.4 (NCH$_2$COOH), 61.9 (CHC$\underline{H}_2$), 57.1 (NC$\underline{H}_2$COOH), 56.5 (N(C$\underline{H}_2$COOH)$_2$), 53.59 (CH$_2$, —N(CH$_2$)$_2$ cycle), 28.6 (CH, cycle) 27.6, (CH$_2$, —CH (CH$_2$)$_2$, cycle).

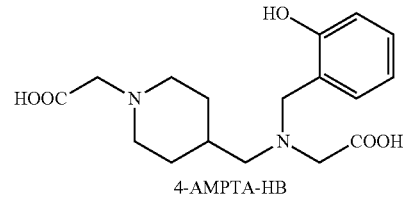 [SMILES: O=C(O)CN1CCC(CN(CC(=O)O)Cc2ccccc2O)CC1]

4-AMPTA-HB

Synthesis of 4-(N-o-hydroxybenzyl-aminomethyl) piperidine. 4-aminomethyl piperidine (500 ml, 4.17 mmol) and salicylaldehyde (435 ml, 4.17 mmol) in CH$_3$OH (5 mL) were stirred for 3 hours at ambient temperature, and then NaBH$_4$ (347 mg, 8.34 mmol) was added in an ice bath for 2 hours and the solvent was evaporated at reduced pressure. The solution was redissolved with 25 mL of AcOEt and washed with 3×10 mL of H$_2$O, then anhydrified with Na$_2$SO$_4$. The organic solution was then filtered through a pleated filter and the solvent evaporated in the rotavapor, thus obtaining N-(o-hydroxybenzyl)-4-aminomethyl piperidine (328 mg, 45%). ESI+ MS: m/z. 221.2 (M+H$^+$). $^1$H NMR (CDCl$_3$, 500 MHz), δ(ppm): 7.16, 7.17, 7.19, (t, 1H, ring), 6.82-7.00 (m, 1H, ring), 6.77-7.00 (m, 1H, ring), 7.19 (s, 1H, ring), 3.10, 3.12, (d, 2H, cycle), 2.62, 2.64, (m, 2H, cycle), 2.56, 2.60, (m, 2H, CH$_2$—NH$_2$), 1.20, 1.23 (m, 1H, cycle). $^{13}$C NMR (CDCl$_3$, 500 MHz), δ(ppm): 159.0 (C, ring), 129.5 (CH, ring), 129.0 (CH, ring), 123.3 (C, ring), 119.2 (CH, ring), 117.1 (CH, ring), 53.7, 55.9, (CH$_2$, CH$_2$—NH), 47.0, 32.0, (CH$_2$, ring), 37.0, (CH, ring).

Synthesis of 4-AMPDA-HB-(OtBu)$_2$. K$_2$CO$_3$ (622 mg, 4.5 mmol) was added to a solution of 4-(N-o-hydroxybenzyl-aminomethyl) piperidine (328 mg, 1.49 mmol) and tert-butyl bromoacetate (437 ml, 2.98 mmol) in CH$_3$CN (10 mL). The mixture was allowed to react while stirring for 2 hours at ambient temperature; after removing the solvent at reduced pressure, the crude product was purified by means of column chromatography (SiO$_2$, acetone/hexane 1:99>20: 80), thus obtaining the product at 40% yield. ESI+ MS: m/z. 449 (M+H$^+$). $^1$H NMR (CDCl$_3$, 500 MHz), δ(ppm): 7.18 (t, 1H, CH$^{Ar}$), 6.96 (d, 1H, CH$^{Ar}$), 6.85 (d, 1H, CH$^{Ar}$), 6.78 (t, 1H, CH$^{Ar}$), 3.79 (s, 2H, CH$_2$), 3.22 (s, 2H, CH$_2$), 3.12 (s, 2H, CH$_2$), 2.93 (d, 2H, CHCH$_2$N), 2.44 (m, 2H, CH$_2^{pip}$), 2.18 (m, 3H, CH+ CH$_2^{pip}$), 1.74 (m, 2H, CH$_2^{pip}$), 1.47 (s, 18H, CH$_3$). $^{13}$C NMR (CDCl$_3$, 500 MHz) δ(ppm): 170.7 (CO), 158.2 (C$^{Ar}$OH), 122.6 (CH$^{Ar}$), 122.1 (CH$^{Ar}$), 119.9 (CH$^{Ar}$), 117.1 (CH$^{Ar}$), 112.1 (C$^{Ar}$), 82.7 (C), 66.8 (CH$_2$), 60.8 (CH$_2$), 59.4 (CH$_2$), 56.7 (CH$_2$), 53.7 (CH$_2$), 33.9 (CH), 30.9 (CH$_2$), 28.9 (CH$_3$).

Synthesis of 4-AMPDA-HB. 4-AMPDA-HB(Ot-Bu)$_2$ (247 mg) was reacted with TFA (10 mL) in CH$_2$Cl$_2$ (10 mL) for one night at ambient temperature. After removing the solvent at reduced pressure, the species was dissolved in CH$_3$CN (1 mL) and precipitated in diethyl ether. The solid was centrifuged and washed 3 times with diethyl ether, thus obtaining a crude reaction product which was purified by means of semi-preparative HPLC-MS using CH$_3$OH 0.1% TFA and H$_2$O 0.1% TFA as eluents. The 4-AMPDA-HB peak came out at minute 1.8 (32 mg, 17%).

ESI+ MS: m/z. 337.3 (M+H$^+$). $^1$H NMR (D$_2$O, 500 MHz), δ(ppm): 7.41 (t, 1H, CH), 7.35 (d, 1H, CH$^{Ar}$), 7.01 (m, 1H, 2×CH$^{Ar}$), 3.88 (s, 2H, CH$_2$), 3.81 (s, 2H, CH$_2$), 3.57 (d, 2H, CHCH$_2$N), 3.34 (s, 2H, CH$_2$), 3.26 (m, 2H, CH$_2^{pip}$), 2.28 (m, 1H, CH), 2.15 (m, 2H, CH$_2^{pip}$), 1.65 (m, 2H, CH$_2^{pip}$). $^{13}$C NMR (D$_2$O, 500 MHz) δ(ppm): 170.5, 169.5, (C, COOH), 133.3, 130.0, 123.1, 121.7, 116.5, 113.3, (CH, ring), 61.0, 58.4, (CH$_2$, CH$_2$COOH), 56.8, (CH$_2$, CH$_2$N), 53.5, (CH$_2$, cycle), 49.7 (CH$_2$, CH$_2$N), 30.0, (CH, cycle), 27.4 (CH$_2$, cycle).

trans-CDHB-DA

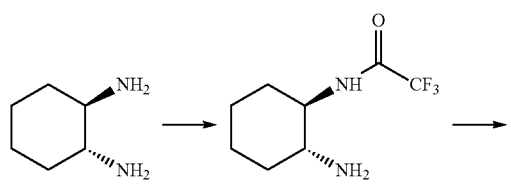

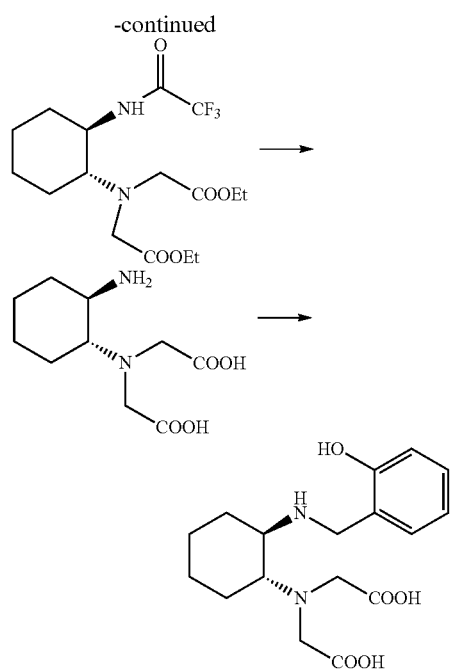

trans-diaminocyclohexane-N-trifluoroacetamide. trans-diaminocyclohexane (500 mg, 4.38 mmol) was dissolved in dioxane (20 mL). The solution was cooled to 5° C. and ethyl trifluoroacetate (0.52 mL, 4.38 mmol) was progressively added. After removing the ice bath, the mixture was stirred at ambient temperature for one night. The solvent was then evaporated at reduced pressure and the residue was suspended in H$_2$O (50 mL) and extracted with EtOAc (5×10 mL). The joined organic phases were dried with anhydrous MgSO$_4$, filtered and evaporated. The crude product (584 mg) was used for the next step without further purification. $^1$H NMR (500 MHz, 25° C., CDCl$_3$), δ (ppm): 6.62 (bs, 1H, NH), 3.39 (m, 1H, CHNH), 2.43 (m, 1H, CHNH$_2$), 2.08 (m, 1H, NHCHCHH'), 1.91 (1H, NH$_2$CHCHH'), 1.68 (m, 2H, NHCHCH$_2$CH$_2$), 1.4-1.0 (m, 6H, NHCHCHH'+NH$_2$CHCHH'+NH$_2$CHCH$_2$CH$_2$+NH$_2$). $^{13}$C NMR (125 MHz, 25° C., CDCl$_3$), δ (ppm): 157.3 (q, $^2J_{CF}$=36.4 Hz, CO), 115.9 (q, $^1J_{CF}$=286.7 Hz, CF$_3$), 57.0 (CHNH), 54.7 (CHNH$_2$), 36.2 (NH$_2$CHCH$_2$), 31.6 (NHCHCH$_2$), 24.9 (NHCHCH$_2$CH$_2$), 24.7 (NH$_2$CHCH$_2$CH$_2$). ESI$^+$ MS: m/z 211.2 [M+H$^+$], calc. for [C$_8$H$_{14}$F$_3$N$_2$O]$^+$=211.11 g/mol.

trans-diaminocyclohexane-N-trifluoroacetamide-N'-bis (ethyl acetate). trans-diaminocyclohexane-N-trifluoroacetamide (580 mg, 2.76 mmol) was solubilized in MeCN (20 mL). K$_2$CO$_3$ (1.14 g, 8.28 mmol) was added, followed by ethyl bromoacetate (1.46 mL, 13.24 mmol), and the reaction mixture was stirred at reflux temperature for one night. The solvent was evaporated at reduced pressure, and the residue was suspended in EtOAc (40 mL) and washed with H$_2$O (2×20 mL) and saturated aqueous NaCl (20 mL). The organic phase was dried on anhydrous Na$_2$SO$_4$, filtered and evaporated under vacuum. The crude product (731 mg) was used in the next reaction without further purification. ESI$^+$ MS: m/z 383.2 [M+H$^+$], calc. for [C$_{16}$H$_{26}$F$_3$N$_2$O$_5$]$^+$=383.18 g/mol.

trans-diaminocyclohexane-N-bis(acetate). trans-diaminocyclohexane-N-trifluoroacetamide-N'-bis(ethyl acetate) (50 mg, 0.13 mmol) was dissolved in THF (4 mL). An aqueous solution 1 M of LiOH (4 mL) was added and the biphasic mixture obtained was heated to 50° C. and stirred vigorously for 2 hours. The solvents were evaporated at reduced pressure, the residue was redissolved in H$_2$O (5 mL) and the pH corrected to approximately 7 using HCl 1 M. The resulting solution was lyophilized and the crude product thus obtained was used for the subsequent synthesis without further purification. ESI$^+$ MS: m/z 231.3 [M+H$^+$], calc. for [C$_{10}$H$_{19}$N$_2$O$_4$]$^+$=231.13 g/mol.

trans-diaminocyclohexane-N-bis(acetate)-N'-o-hydrozybenzyl (CDHB-DA). trans-diaminocyclohexane-N-bis(acetate) (50 mg, 0.22 mmol) was dissolved in anhydrous MeOH (2 mL). Salicylaldehyde (0.050 mL, 0.47 mmol) was then added dropwise and the reaction mixture was stirred at ambient temperature for 1 h. The solution was then cooled to 0° C. and NaBH$_4$ (83 mg, 2.20 mmol) was added in small portions. The resulting suspension was stirred for one night at ambient temperature, after which H$_2$O (5 mL) was added at 0° C. and the mixture was stirred for a further 30 min. The solvents were evaporated at reduced pressure and the residue was resuspended in H$_2$O (10 mL), filtered using a membrane filter and the filtrate was finally lyophilized. The product was purified by means of preparative HPLC-MS and obtained as a white solid (34 mg, 78%). $^1$H NMR (500 MHz, 25° C., D$_2$O), δ (ppm): 7.30 (m, 2H, CHCHCOH+CHCCH$_2$), 6.92 (m, 2H, CHCOH+CHCHCCH$_2$), 4.34 (d, $^2$J$_{HH'}$=13.2 Hz, 1H, NCHH'Ar), 4.05 (d, $^2$J$_{HH'}$=13.2 Hz, 1H, NCHH'Ar), 3.6-3.1 (bm, 4H, CH$_2$CO), 2.90 (m, 1H, CHNH), 2.53 (m, 1H, CHN), 2.32 (m, 1H, CHH'$^{CyHex}$), 1.92 (m, 1H, CHH'$^{CyHex}$), 1.73 (m, 2H, 2×CHH'$^{CyHex}$), 1.38 (m, 1H, CHH'CyHex), 1.17 (m, 3H, 3×CHH'$^{CyHex}$). $^{13}$C NMR (125 MHz, 25° C., D$_2$O), δ (ppm): 175.7 (COOH), 155.0 (COH), 131.6 (CHCCH$_2$), 131.5 (CHCHCOH), 120.6 (CHCHCCH$_2$), 117.5 (CCH$_2$), 115.2 (CHCOH), 63.2 (CHN), 57.0 (CHNH), 44.2 (NCH$_2$Ar), 27.1 (CH$_2$$^{CyHex}$), 24.5 (CH$_2$$^{CyHex}$) 24.1 (CH$_2$$^{CyHex}$), 23.3 (CH$_2$$^{CyHex}$). ESI$^+$ MS: m/z 337.3 [M+H$^+$], calc. for [C$_{17}$H$_{25}$N$_2$O$_5$]$^+$=337.18 g/mol.

trans-CDDA-HB

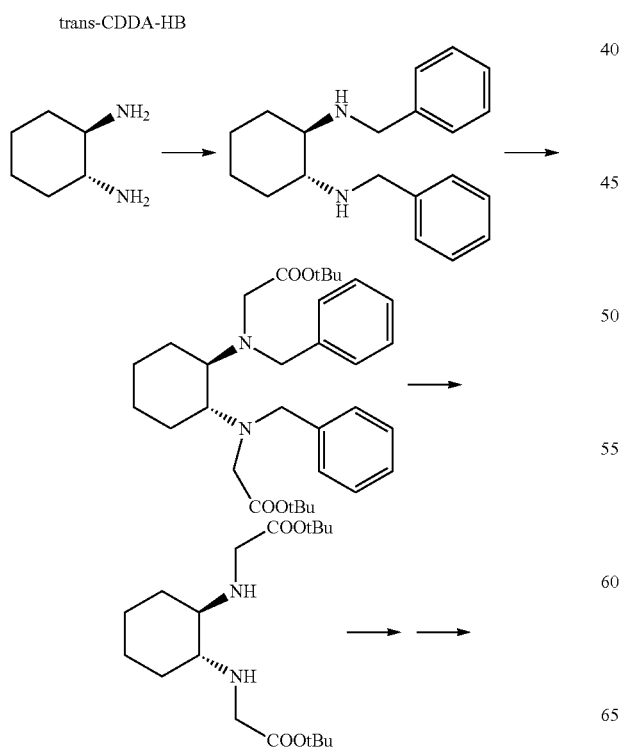

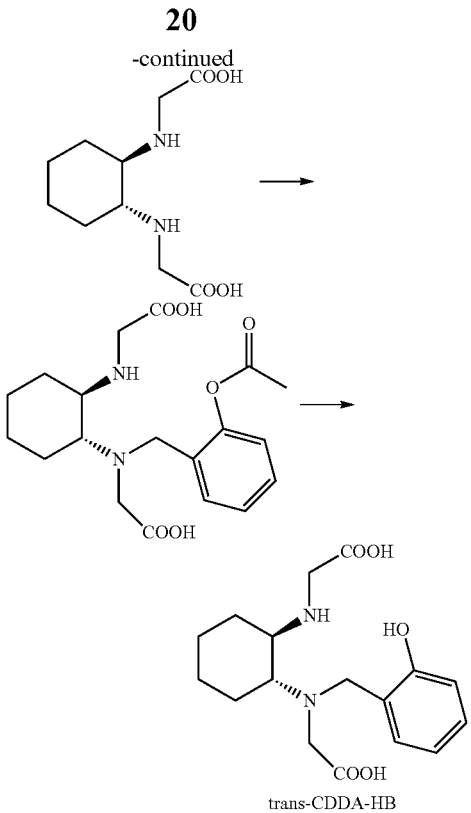

trans-CDDA-HB trans-N,N'-dibenzyl diaminocyclohexane. trans-diaminocyclohexane (500 mg, 4.38 mmol) was dissolved in anhydrous MeOH (20 mL). Salicylaldehyde (1.34 mL, 13.14 mmol) was added dropwise and the reaction mixture was stirred at ambient temperature for 1 h. The solution was then cooled to 0° C. and NaBH$_4$ (663 mg, 17.52 mmol) was added in small portions. The resulting suspension was stirred for one night at ambient temperature, after which H$_2$O (5 mL) was added at 0° C. and the mixture was stirred for a further 30 min. The solvents were evaporated at reduced pressure and the residue was resuspended in EtOAc (20 mL) and washed with H$_2$O (2×10 mL) and saturated aqueous NaCl (10 mL). The organic phase was dried on anhydrous Na$_2$SO$_4$, filtered and evaporated under vacuum, and the desired product was obtained in a sufficiently pure form as a yellow oil (658 mg, 51%). $^1$H NMR (500 MHz, 25° C., CDCl$_3$), δ (ppm): 7.4-7.2 (m, 10H, Ph), 3.92 (d, $^2$J$_{HH'}$=13.0 Hz, 2H, NCHH'Ph), 3.78 (d, $^2$J$_{HH'}$=13.0 Hz, 2H, NCHH'Ph), 2.72 (m, 2H, CHNH), 1.80 (m, 2H, NHCHCHH'), 1.55 (m, 2H, NHCHCHH'), 1.35 (m, 4H, NHCHCH$_2$CH$_2$). $^{13}$C NMR (125 MHz, 25° C., CDCl$_3$), δ (ppm): 142.4 (C$^{Ph}$), 130.7, 130.1, 129.0 (3×CH$^{Ph}$), 61.3 (CHNH), 31.7 (NHCHCH$_2$), 27.3 (NHCHCH$_2$CH$_2$), ESI$^+$ MS: m/z 295.4 [M+H$^+$], calc. for [C$_{20}$H$_{27}$N$_2$]$^+$=295.22 g/mol.

trans-N,N'-dibenzyl diaminocyclohexane-N,N'-bis(tert-butyl acetate). trans-N,N'-dibenzyl diaminocyclohexane (500 mg, 1.70 mmol) was solubilized in MeCN (10 mL). K$_2$CO$_3$ (704 g, 5.09 mmol) was added, followed by tert-butyl bromoacetate (0.55 mL, 3.74 mmol), and the reaction mixture was stirred at reflux temperature for one night. The solvent was evaporated at reduced pressure, and the residue was suspended in EtOAc (20 mL) and washed with H$_2$O (10 mL) and saturated aqueous NaCl (2×10 mL). The organic phase was dried on anhydrous MgSO$_4$, filtered and evaporated under vacuum. The crude product (876 mg) was used in the next reaction without further purification. ESI+ MS: m/z 523.6 [M+H+], calc. for $[C_{32}H_{47}N_2O_4]^+$=523.73 g/mol.

trans-diaminocyclohexane-N,N'-bis(tert-butyl acetate). trans-N,N'-dibenzyl diaminocyclohexane-N,N'-bis(tert-butyl acetate) (876 mg, 0.1.68 mmol) was dissolved in MeOH (40 mL). 10% Pd/C (88 mg) suspended in MeOH (1 mL) was added, the suspension was saturated with $H_2$ by means of bubbling for 10 min, 3 vacuum/$H_2$ cycles were applied and the mixture was stirred at ambient temperature for one night under an $H_2$ atmosphere. The suspension was then filtered through Celite® and the filtrate was evaporated at reduced pressure. The crude product (520 mg) was obtained as a beige solid and used for the subsequent procedure without further purification steps. ESI+ MS: m/z 343.3 [M+H+], calc. for $[C_{18}H_{35}N_2O_4]^+$=343.48 g/mol.

trans-N,N'-dibenzyl diaminocyclohexane-N,N'-bis(acetate). trans-diaminocyclohexane-N,N'-bis(tert-butyl acetate) (520 mg, 1.52 mmol) and triisopropylsilane (3 drops) were dissolved in DCM (10 mL), TFA (10 mL) was added and the mixture obtained was stirred at ambient temperature for one night. The solvents were evaporated at reduced pressure, and the residue was redissolved in TFA (1 mL) and precipitated in diethyl ether. The solid was centrifuged and washed 3 times with diethyl ether and dried under vacuum (white solid, 331 mg). The crude product thus obtained was used for the subsequent synthesis without further purification. ESI+ MS: m/z 231.4 [M+H+], calc. for $[C_{10}H_{19}N_2O_4]^+$=231.26 g/mol.

trans-diaminocyclohexane-N—(O-acetyl-o-hydroxybenzyl)-N,N'-bis(acetate). trans-N,N'-diaminocyclohexane-N,N'-bis(acetate) (0.51 mmol theoretical) was solubilized in MeCN (10 mL). $K_2CO_3$ (70 mg, 0.51 mmol) was added, followed by O-acetyl-2-bromomethylphenyl (117 mg, 0.51 mmol), and the reaction mixture was stirred at reflux temperature for one night. The solvent was evaporated at reduced pressure, and the residue was suspended in EtOAc (20 mL) and extracted with $H_2O$ (2×10 mL). The aqueous phase was lyophilized and the crude product obtained was used immediately for the final deprotection reaction. ESI+ MS: m/z 379.3 [M+H+], calc. for $[C_{19}H_{27}N_2O_6]^+$=379.19 g/mol.

trans-diaminocyclohexane-N-(o-hydroxybenzyl)-N,N'-bis(acetate). trans-diaminocyclohexane-N—(O-acetyl-o-hydroxybenzyl)-N,N'-bis(acetate) (0.51 mmol theoretical) was dissolved in THF (7 mL). An aqueous solution 1 M of NaOH (7 mL) was added and the mixture obtained was heated to 50° C. and stirred vigorously for 3 hours. The solvents were evaporated at reduced pressure and the residue was purified by means of preparative HPLC-MS and obtained as a white solid (5 mg). $^1$H NMR (500 MHz, 25° C., $D_2O$), δ (ppm): 7.46 (m, 2H, 2×$CH^{Ar}$), 7.36 (m, 2H, 2×$CH^{Ar}$), 4.45 (d, $^2J_{HH}$=12.9 Hz, 1H, NCHH'Ar), 4.08 (d, $^2J_{HH}$=12.9 Hz, 1H, NCHH'Ar), 3.94 (d, $^2J_{HH}$=16.4 Hz, 1H, NCHH'CO), 3.64 (d, $^2J_{HH}$=16.4 Hz, 1H, NCHH'CO), 3.34 (m, 1H, C$\underline{H}$NH), 3.10 (m, 1H, CHN), 2.21 (m, 1H, C$\underline{H}$H'$^{CyHex}$), 1.88 (m, 1H, CHH'$^{CyHex}$), 1.78 (m, 2H, 2×C$\underline{H}$H'$^{\overline{CyHex}}$), 1.65 (m, 1H, CHH'$^{\overline{CyHex}}$), 1.2-1.0 (m, 3H, 3×CH$\underline{H}$'$^{CyHex}$). $^{13}$C NMR (125 MHz, 25° C., $D_2O$), δ (ppm): 176.2 (COOH), 155.0 (COH), 131.4 ($\underline{C}$HCCH$_2$), 131.2 ($\underline{C}$HCHCOH), 128.1 ($\underline{C}$HCHCCH$_2$), 126.4 ($\underline{C}$CH$_2$), 122.1 ($\underline{C}$HCOH), 63.9 (CHN), 57.6 (CHNH), 48.5 (N$\underline{C}$H$_2$Ar), 31.0 ($CH_2^{CyHex}$), 25.5 ($CH_2^{CyHex}$), 24.6 ($CH_2^{CyHex}$), 24.3 ($CH_2^{CyHex}$). ESI+ MS: m/z 337.3 [M+H+], calc. for $[C_{17}H_{25}N_2O_5]^+$=337.18 g/mol.

The invention claimed is:

1. A coordination complex comprising $[Al^{18}F]^{2+}$ and a compound selected from the R and S isomers of 2-AMPDA-HB and 3-AMPDA-HB:

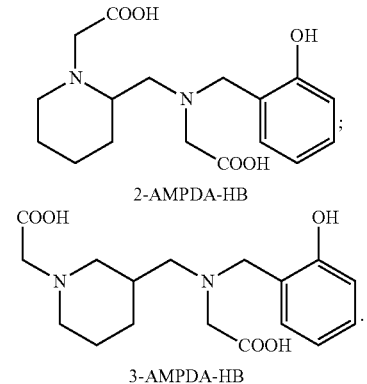

2-AMPDA-HB

3-AMPDA-HB

2. A labeled biomolecule, conjugated with a coordination complex according to claim 1.

3. The labeled biomolecule of claim 2, wherein said labeled biomolecule is selected from the group consisting of antibodies, antibody fragments, nanobodies and affibodies.

4. A Positron Emission Tomography (PET) imaging method for the diagnosis of a disease in a subject, comprising administering to said subject the coordination complex of claim 1.

5. The PET imaging method of claim 4, wherein said disease is a tumor.

6. A method of labelling a compound selected from R and S isomers of 2-AMPDA-HB and 3-AMPDA-HB

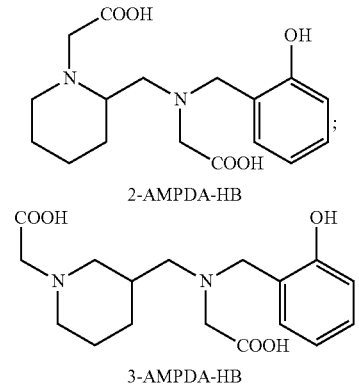

2-AMPDA-HB

3-AMPDA-HB with $^{18}$F, comprising contacting said compound with $[Al^{18}F]^{2+}$ in an aqueous medium.

7. The method of claim 6, wherein said compound is conjugated with a biomolecule.

8. The method of claim 7, wherein said biomolecule is selected from the group consisting of antibodies, antibody fragments, nanobodies and affibodies.

9. The method of claim 6, wherein the aqueous medium has a pH comprised between 3.5 and 6.

10. The method of claim 6, wherein the aqueous medium has a temperature comprised between 20° and 80° C.

11. The labeled biomolecule of claim 2, wherein said labeled biomolecule is selected from the group consisting of proteins, peptides, carbohydrates, phospholipids, fatty acids, nucleosides, deoxynucleosides, nucleotides, and deoxynucleotides.

12. A Positron Emission Tomography (PET) imaging method for the diagnosis of a disease in a subject, comprising administering to said subject the labeled biomolecule of claim 2.

13. The PET imaging method of claim 12, wherein said disease is a tumor.

14. The PET imaging method of claim 12, wherein said biomolecule is selected from the group consisting of proteins, peptides, carbohydrates, phospholipids, fatty acids, nucleosides, deoxynucleosides, nucleotides and deoxynucleotides, antibodies, antibody fragments, nanobodies and affibodies.

* * * * *